United States Patent
Castellin et al.

(10) Patent No.: US 8,557,981 B2
(45) Date of Patent: Oct. 15, 2013

(54) PROCESS FOR THE SYNTHESIS OF 4H-IMIDAZO [1,5-A] [1,4] BENZODIAZEPINES, IN PARTICULAR MIDAZOLAM AND SALTS THEREOF

(75) Inventors: Andrea Castellin, Mestrino (IT); Michele Maggini, Selvazzano Dentro (IT); Paola Donnola, Padua (IT)

(73) Assignee: F.I.S. Fabbrica Italiana Sintetici S.p.A., Alte di Montecchio Maggiore (IT)

( * ) Notice: Subject to any disclaimer, the term of this patent is extended or adjusted under 35 U.S.C. 154(b) by 226 days.

(21) Appl. No.: 13/099,820

(22) Filed: May 3, 2011

(65) Prior Publication Data

US 2011/0275799 A1 Nov. 10, 2011

(30) Foreign Application Priority Data

May 4, 2010 (IT) .................................. MI10A0777

(51) Int. Cl.
*C07D 487/12* (2006.01)
(52) U.S. Cl.
USPC ........................................ 540/562; 548/334.5
(58) Field of Classification Search
USPC ........................................ 540/562; 548/334.5
See application file for complete search history.

(56) References Cited

U.S. PATENT DOCUMENTS

| 4,280,957 A | 7/1981 | Walser et al. |
| 5,693,795 A | 12/1997 | Bender et al. |
| 6,262,260 B1 | 7/2001 | Dhaon |
| 6,512,114 B1 | 1/2003 | Dhaon et al. |

FOREIGN PATENT DOCUMENTS

GB  1 527 131 A  10/1978

*Primary Examiner* — Brenda Coleman
(74) *Attorney, Agent, or Firm* — Dickstein Shapiro LLP

(57) ABSTRACT

The present invention refers to a process for the preparation of 4H-imidazo[1,5-a][1,4]benzodiazepines, in particular Midazolam, through an efficient and selective decarboxylation reaction of the derivative compound of the 5-aminomethyl-1-phenyl-1H-imidazole-4-carboxylic acid of formula (II)

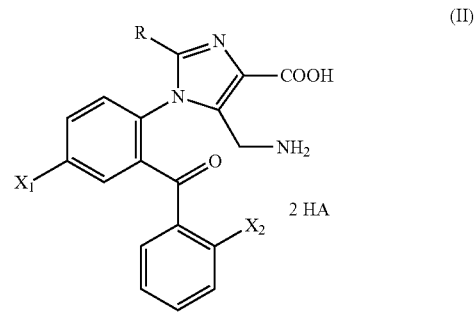

avoiding the formation of the 6H-imidazo[1,5-a][1,4]benzodiazepines by-products and the ensuing process for the isomerization of a 4H-imidazo[1,5-a][1,4]benzodiazepine product.

15 Claims, 1 Drawing Sheet

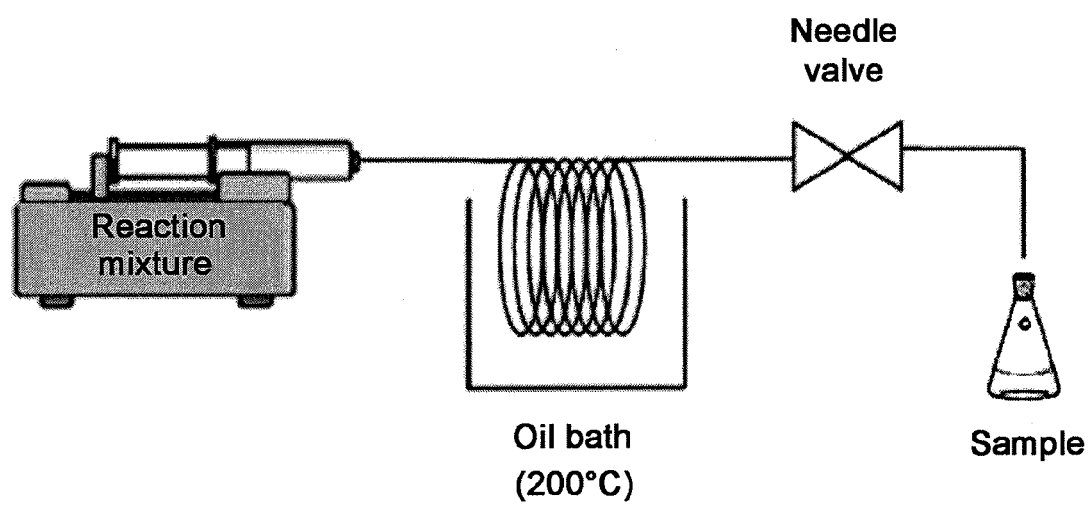

PROCESS FOR THE SYNTHESIS OF 4H-IMIDAZO [1,5-A] [1,4] BENZODIAZEPINES, IN PARTICULAR MIDAZOLAM AND SALTS THEREOF

TECHNICAL FIELD OF THE INVENTION

A process for the preparation of 4H-imidazo[1,5-a][1,4]benzodiazepines and in particular for the synthesis of Midazolam forms an object of the present invention.

STATE OF THE ART 4H-imidazo[1,5-a][1,4]benzodiazepines or, more simply, imidazobenzodiazepines, are a class of benzodiazepines having the general formula (I),

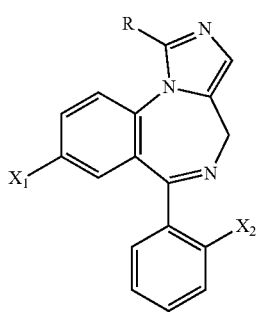

(I)

wherein the 1,4-diazepine ring is fused with a 1,3-imidazole ring. The main compounds part of the 4H-imidazo[1,5-a][1,4]benzodiazepines are Midazolam of formula (IV):

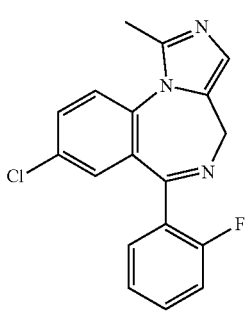

(IV)

an active ingredient currently commercially available as a hydrochloride salt under the name of Versed or Hypnovel for anaesthetic and sedative use and the maleate salt currently commercially available under the name Dormicum or Flormidal.

Other important compounds are Climazolam of formula (VII):

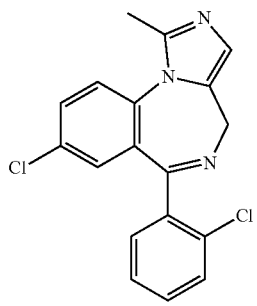

(VII)

Imidazenil of formula (VIII):

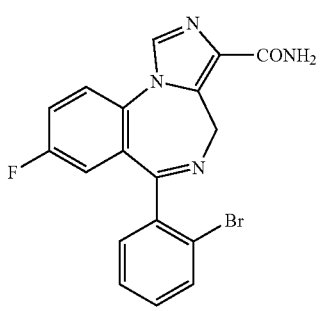

(VIII)

1-Hydroxymidazolam of formula (IX):

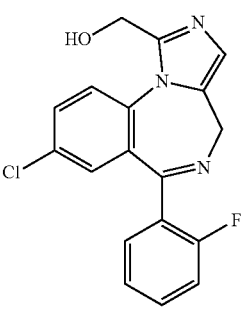

(IX)

and Desmethyl midazolam of formula (X):

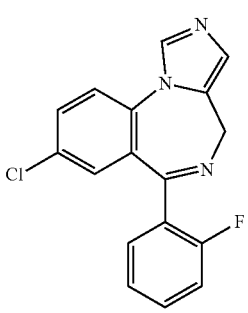

(X)

all these being biologically active substances and having psychotropic and sedative action.

The synthesis of the Midazolam as described in U.S. Pat. No. 4,280,957 of Hoffmann-La Roche provides for the decarboxylation reaction of the 8-chloro-6-(2-fluorophenyl)-1-methyl-4H-imidazo[1,5-a][1,4]benzodiazepine-3-carboxylic acid of formula (VI) according to the following scheme:

Scheme I:

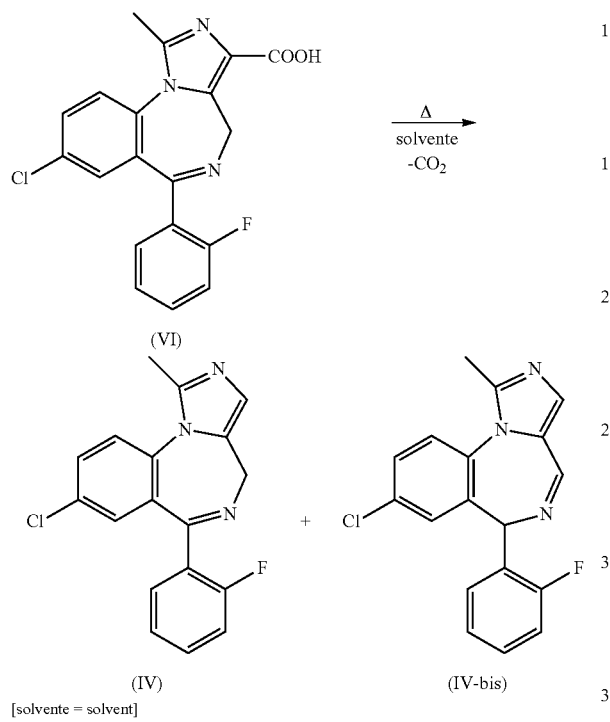

[solvente = solvent]

The process for preparing the intermediate (VI) via basic hydrolysis of the corresponding ester is described in such patent publication and it is well known in the art.

The thermal decarboxylation reaction in high boiling solvent such as mineral oil at 230° C. for 5 min results in a mixture of products of Midazolam of formula (IV) and of Isomidazolam of formula (IV-bis), a non-pharmacologically active isomer, at a 80:20 ratio. The two products are separated by chromatography.

At industrial level, the formation of the Isomidazolam isomer impurity requires a further isomerisation reaction performed on the mixture of the two compounds to convert the isomer into the active product. The reaction mixture obtained from the thermal decarboxylation is thus subjected to basic treatment under the action of KOH in EtOH followed by an acid treatment which thus provides a mixture of Midazolam-Isomidazolam at a 95:5 ratio. The final removal of the Isomidazolam impurity from the product occurs through crystallisation of the product from AcOEt and EtOH. In order to limit this isomerisation treatment, in the subsequent U.S. Pat. No. 5,693,795 of Hoffmann-La Roche dated 1999, there is described a process for performing the decarboxylation of the compound of formula (VI) in n-butanol in a continuous tubular reactor with a 4 minutes permanence period with a yield between 47-77%. However, the reaction, performed at high temperature and pressure (280° C., 100 bars) results in the formation of a considerable percentage of Isomidazolam (85: 15 Midazolam/Isomidazolam ratio) which still requires the basic isomerisation step.

Lastly, in U.S. Pat. No. 6,512,114 of Abbott Laboratories there is described the decarboxylation of the compound of formula (VI) in mineral oil or in N,N-Dimethylacetamide (DMA) at 160-230° C. for at least 3 hours obtaining a 3/1 to 6/1 Midazolam/Isomidazolam ratio with a yield of isolated product equal to just 54%.

Though performed using dedicated apparatus and in extreme conditions, the prior art processes do not allow selectively performing the decarboxylation reaction of the intermediate (VI) to Midazolam thus requiring a further synthetic passage followed by crystallisation with ensuing reduction of the overall yield.

SUMMARY OF THE INVENTION

Thus, the problem addressed by the present invention is that of providing an alternative process for the preparation of 4H-imidazo[1,5-a][1,4]benzodiazepines, through a new intermediate capable of at least partly overcoming the previously mentioned drawbacks with reference to the prior art.

Such problem is overcome by a process for the synthesis of 4H-imidazo[1,5-a][1,4]benzodiazepines as outlined in the attached claims, the definitions thereof forming an integral part of the present description. Further characteristics and advantages of the process according to the invention shall be apparent from the following description of preferred embodiments, provided purely by way of non-limiting example.

BRIEF DESCRIPTION OF THE FIGURES

By way of example:

FIG. 1 shows a schematic representation of the microreactor (MR) in PTFE® used in an embodiment of the thermal decarboxylation reaction.

DETAILED DESCRIPTION OF THE INVENTION

The present invention relates to a process for the preparation of 4H-imidazo[1,5-a][1,4]benzodiazepine of formula (I) or a salt thereof:

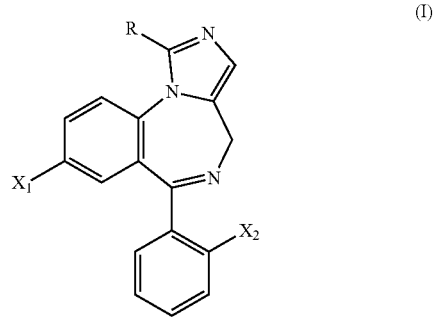

wherein R is selected from the group consisting of H, CH3, CH2OH and C2H5; X1 and X2 are independently selected from H and halogen, starting from the intermediate of formula (III):

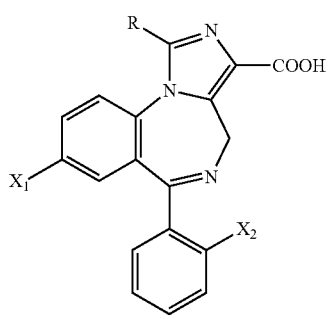

(III)

wherein R, X1 and X2 have the same meaning indicated above.

It has been surprisingly found that performing the decarboxylation reaction of the derivative compound of the 5-aminomethyl-1-phenyl-1H-imidazole-4-carboxylic acid having formula (II):

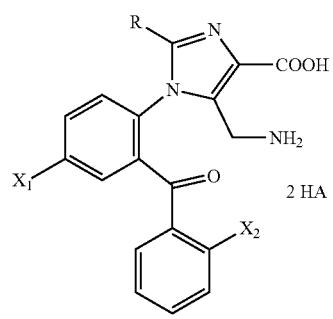

(II)

2 HA wherein HA is an inorganic acid, obtainable through acid hydrolysis of the compound of formula (III), allows easily obtaining and with good yields the product of formula (I) thus avoiding the formation of isomers such as 6H-imidazole[1,5-a][1,4]benzodiazepines of formula (I-bis):

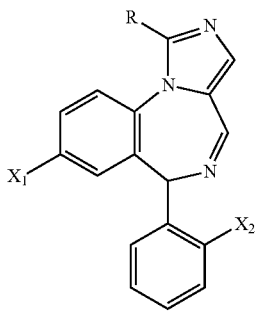

(I-bis)

and thus the need for performing the step of isomerisation of the mixture obtained from the decarboxylation reaction as well as the subsequent crystallisation of the product to eliminate the residual isomer impurity. Furthermore, the conditions required to perform the decarboxylation reaction of the compound of formula (II) neither provide for the use of high pressures, thus nor that of apparatus specific for the purpose, thus allowing performing the reaction both in batch and continuous or semi-continuous mode in common industrial reactors or industrial microreactors.

The derivative compound of the 5-aminomethyl-1-phenyl-1H-imidazole-4-carboxylic acid having formula (II) can be easily prepared through acid hydrolysis of the derivative of the 4H-imidazo[1,5-a][1,4]benzodiazepine-3-carboxylic acid having formula (III) according to the scheme 2 below:

Scheme 2

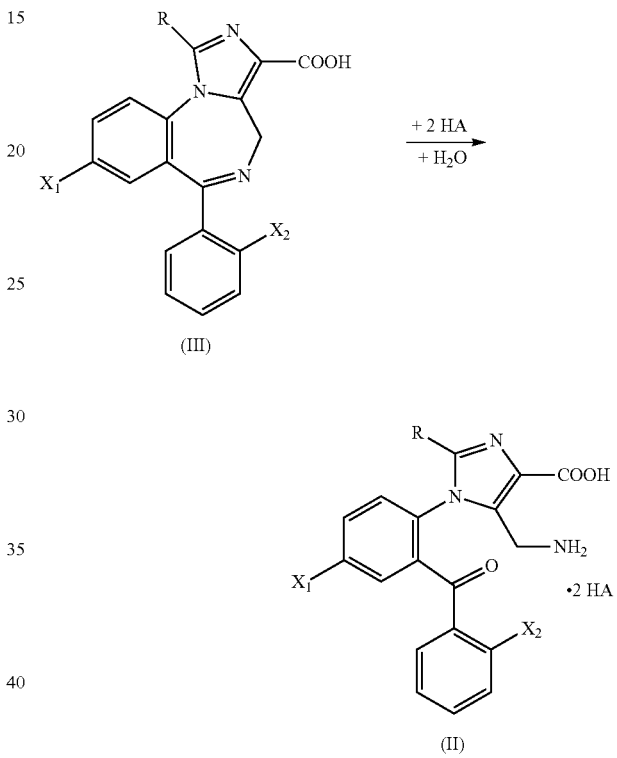

(III)

+ 2 HA
+ H$_2$O

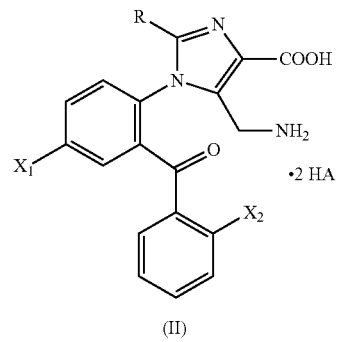

(II)

wherein HA is any inorganic acid such as hydrofluoric, hydrochloric, hydrobromic, hydroiodic, hydrosulfuric, sulphurous, sulphuric, chloric acid etc. The hydrolysis reaction of the compound (III) can thus be easily performed using the HA acid in more or less diluted aqueous solution. In an embodiment, HA is preferably diluted hydrochloric acid and the reaction is performed at ambient temperature by simply dissolving the compound of formula (II) in the HA acid and/or in the presence of alcohol. The product can be conveniently isolated from the reaction mixture through filtration, then it can be washed and dried.

The obtained product contains two molecules of HA acid as shown by the titration with NaOH which has 3 inflection points (one is for the carboxylic function). As a further confirmation of the stoichiometry of the molecule, in the case wherein HA is HCl, there is obtained a titre with AgNO3 which, corrected by the K.F., is 20%).

The decarboxylation reaction of the intermediate of formula (II) to obtain the 4H-imidazo[1,5-a][1,4]benzodiazepine compound of formula (I) or a salt thereof is described in the following scheme 3.

Scheme 3:

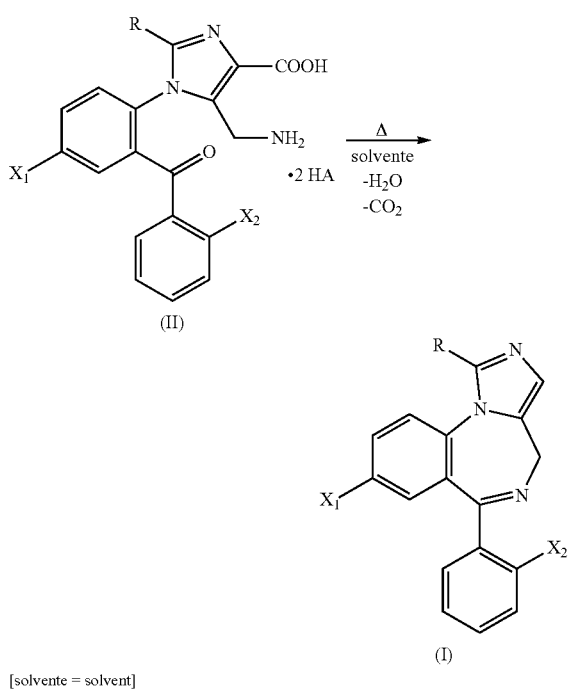

[solvente = solvent]

The fact that the decarboxylation reaction of the compound (II) allows avoiding the formation of the isomer impurity 6H-imidazole[1,5-a][1,4]benzodiazepine of formula (I-bis) is explained by considering that first the intermediate of formula (II-bis) is formed:

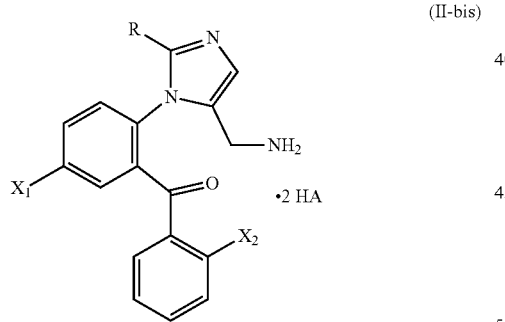

which subsequently cyclises losing water to obtain the 4H-imidazo[1,5-a][1,4]benzodiazepine compound of formula (I) or a salt thereof such as for example the salt with HA. For example, using hydrochloric acid as HA would thus allow directly obtaining the compound of formula (I) as a hydrochloride or this can be treated with a base and then with another acid to obtain another salt of (I). The cyclization reaction of the compound of formula (II-bis) can optionally be facilitated by treating the mixture after decarboxylation with a basic solution or directly with a base.
The decarboxylation reaction of the compound of formula (II) can be performed in a high boiling organic solvent such as for example N-Methylpirrolidinone (NMP), N,N-Dimethylacetamide, Tetralin, mineral oil, etc. at a temperature between 150° C. and 250° C., preferably between 180° C. and 220° C. and more preferably between 195° C. and 205° C.

Hence the reaction is completed within a period of time between 10 minutes and 6 hours, preferably between 30 minutes and 1 hour. Better results in terms of impurity and conversion profile were obtained by using NMP as solvent and carrying out the reaction at about 200° C. for about 1 hour.

In an embodiment, the decarboxylation reaction can be performed both in batch and continuous mode, for example even through a microreactor (MR).

The decarboxylation reaction can thus be performed using the microfluidic device schematically shown in FIG. 1 wherein the solution containing the substrate to be decarboxylated is loaded into a gastight glass syringe mounted on a syringe pump and connected to a pipe spiral made of PTFE®. The reaction channel (L=1 m; V=503 µL) is submerged in a thermostat oil bath at 200° C. A counterpressure valve was arranged downstream of the reaction channel in order to increase the pressure within the microchannel to values such to cause the solubilisation of CO2 in the reaction mixture and the ensuing stabilisation of the flow.

In an embodiment, the process for the synthesis of the compound (I) wherein R is methyl, X1 is chlorine and X2 is Fluorine, i.e. Midazolam, can be described according to scheme 4 indicated below:

Scheme 4:

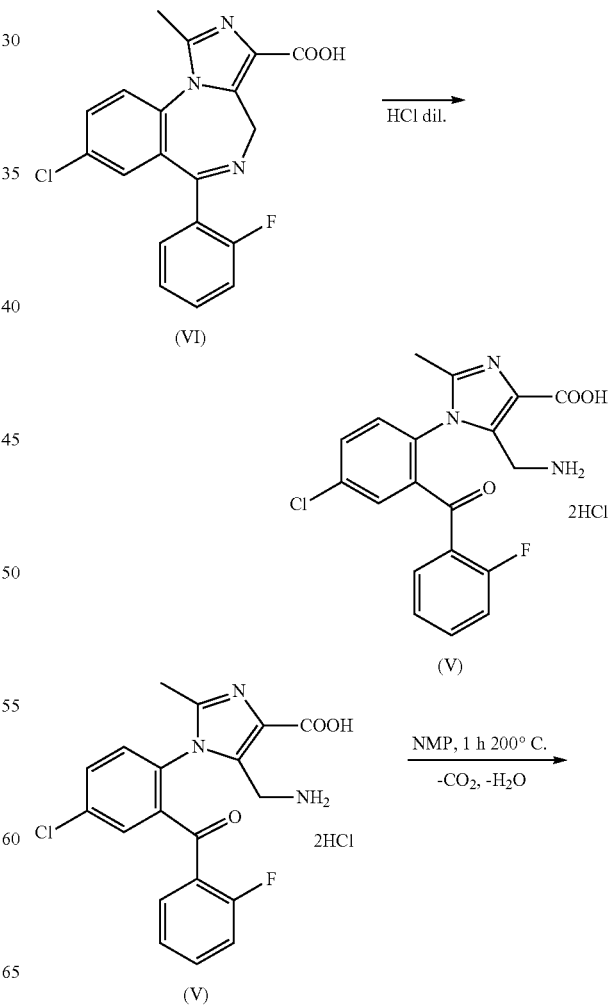

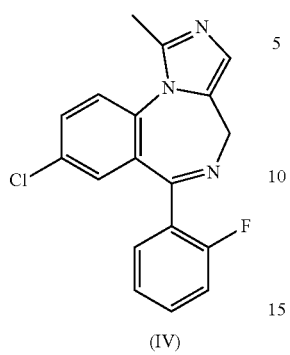

(IV)

In a preferred embodiment, the hydrolysis reaction of the compound of formula (VI) is performed with diluted hydrochloric acid, for example 1M HCl, in the presence of Ethanol obtaining the compound of formula (V), with yields between 80 and 85%, whose analysis have shown to be di-hydrochloride and having a HPLC purity greater than 98% (HPLC A %). The subsequent decarboxylation reaction and simultaneous cyclisation occurs in NMP at 200° C. in about 1 hour.

The decarboxylation reaction can be conveniently performed continuously for example through the previously illustrated microreactor (FIG. 1) using NMP and operating at 200° C.

The experiments conducted through the batch method have revealed that the decarboxylation of the compound of formula (V) is followed by cyclization to obtain Midazolam with molar yields, calculated via HPLC, equal to 82%.

The decarboxylation of the compound of formula (V) was also performed in the microfluidic device made of PTFE® previously illustrated (FIG. 1) hence allowing obtaining Midazolam with molar yields, calculated through HPLC titre, equal to 89% in 30 minutes.

In the following examples there is illustrated the surprising and considerable selective effect of the decarboxylation of the intermediate of formula (II) to give 4H-imidazo[1,5-a][1,4] benzodiazepines.

EXPERIMENTAL PART

Materials and Methods 8-chloro-6-(2-fluorophenyl)-1-methyl-4H-imidazo[1,5-a][1,4]benzodiazepin-3-carboxylic acid of formula (VI) was prepared according to processes known in the art (e.g. U.S. Pat. No. 4,280,957) which comprise the basic hydrolysis of the corresponding ester.

For the reactions performed in the microreactor, the solutions containing the substrates to be decarboxylated were loaded into 5 and 10 mL gastight glass syringes (Hamilton, item n. 81527, 81627) mounted on syringe pumps (KD Scientifics, model KDS100). A pipe made of PTFE® (OD=1.58 mm, ID=0.8 mm, Supelco, item n. 58696-U) was used for making the reaction channel.

A counterpressure valve sold by Swagelok (item n. SS-SS1-VH) was used for regulating the flow within the channel.

Example 1

Synthesis of the Compound of Formula (V)—Example of the Invention

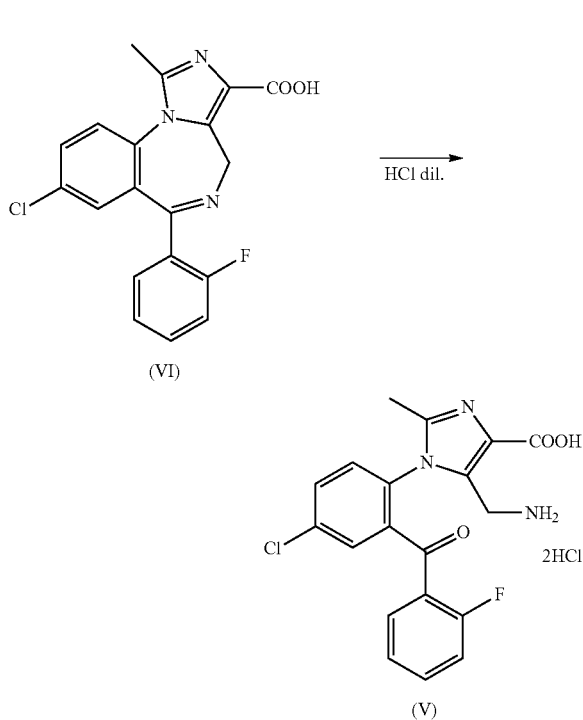

50 g (0.135 mol) of 8-chloro-6-(2-fluorophenyl)-1-methyl-4H-imidazo[1,5-a][1,4]benzodiazepin-3-carboxylic acid of formula (VI) and 250 mL of ethanol were loaded into a two-neck 500 mL flask, equipped with a magnetic stirrer. 40 mL of an aqueous solution of 1 M HCl are dripped in about 10 minutes. The open di-hydrochloride intermediate of formula (V) starts precipitating into the reaction environment already after 3 minutes from the beginning of the addition of the acid solution. The mixture is maintained stirred at RT for 3 hrs and then it is filtered on buckner washing the solid with ethanol. The moist product is dried in an oven under vacuum at 60° C. up to reaching a constant weight. A light yellow crystalline product is obtained (51.5 g, 83% yield). The crude product was used for the decarboxylation without further purifications.

ESI-MS [MeCN+0.1% HCOOH]: m/z 388 (V); 370 (VI).

$^1$H-NMR (250 MHz, CD3OD): 2.52 (s, 3H); 4.27-4.41 (m, 2H); 7.22-8.1 (m, 7H). M.p.: 217° C.

Example 2

Synthesis of Midazolam of Formula (IV)—Performed in Batch—Example of the Invention

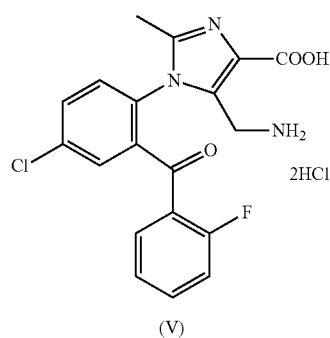

(V)

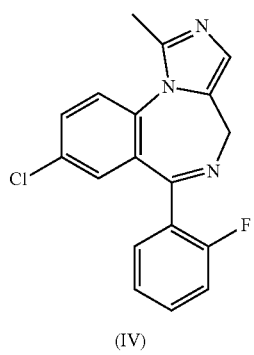

(IV)

30 g (0.065 mol) of 5-(aminomethyl)-1-{(4-chloro-2-[(2-fluorophenyl)carbonyl]phenyl}-2-methyl-1H-imidazole-4-carboxylic acid dihydrochloride of formula (V) and 90 mL of NMP are loaded into a three-neck 250 mL flask, equipped with a magnetic stirrer and coolant. The mass is heated using an oil bath at T=195-203° C. for one hour. Thus, 1 mL of solution is collected for performing HPLC analysis. The reaction product is Midazolam having 82% titre (w/w) (determined via HPLC titre correcting it using the solvent) and it contains 1% of Isomidazolam. The product is extracted using Isopropyl acetate after raising the pH to 10 by adding aqueous Na2CO3.

Example 3

Synthesis of Midazolam of Formula (IV)—Performed in a Micro-Reactor—Example of the Invention

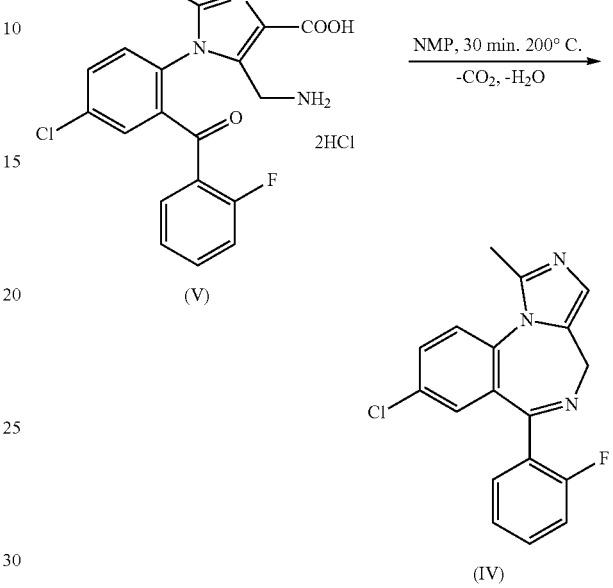

3.22 g (7 mmol) of 5-(aminomethyl)-1-{4-chloro-2-[(2-fluorophenyl)carbonyl]phenyl}-2-methyl-1H-imidazole-4-carboxylic acid dihydrochloride of formula (V) and 10 mL of NMP are loaded into a 10 mL flask equipped with a magnetic stirrer. In order to facilitate the complete solubilisation of the substrate, it is necessary to slightly heat the reaction mixture (about 40° C.) for a few minutes. The solution thus obtained is transferred into a 10 mL gastight glass syringe mounted on a KDS100 syringe pump (FIG. 1) and the flow is regulated at 1.0 mL/h so as to set a residence period of 30 minutes at 200° C. The reaction product is Midazolam having an 89% titre (w/w) (determined via HPLC titre correcting it using the solvent) and containing 3% (w/w) of Isomidazolam.

Example 4

Synthesis of Midazolam of formula (IV)—Comparison of the Invention

A table is reported which summarises the results of the decarboxylation of the compound of formula (V) and (V-bis) (for the latter see Examples 6 and 7) obtained according to some embodiments of the invention and those obtained by way of experiment through the decarboxylation of the intermediate of formula (VI) (process of the prior art) both performed in 3 volumes of NMP at 200° C., both in batch method (Example 4) and in continuous method with the microreactor (MR) made of PTFE of FIG. 1. (Examples 4-1, 4-2, 4-3).

| Example | Substrate | Mode | Solv. | T° C. | t min. | Midazolam (p/p) | Isomidaz. (p/p) |
|---|---|---|---|---|---|---|---|
| 2 | (V) | Batch | NMP | 200 | 60 | 82 | 1 |
| 3 | (V) | MR | NMP | 200 | 30 | 89 | 3 |
| 7 | (V-bis) | Batch | NMP | 200 | 60 | 68 | 3 |
| 4 | (VI) | Batch | NMP | 200 | 60 | 78 | 18 |

-continued

| Example | Substrate | Mode | Solv. | T° C. | t min. | Midazolam (p/p) | Isomidaz. (p/p) |
|---|---|---|---|---|---|---|---|
| 4-1 | (VI) | MR | NMP | 200 | 38 | 81 | 17 |
| 4-2 | (VI) | MR | NMP | 200 | 20 | 77 | 18 |
| 4-3 | (VI) | MR | NMP | 200 | 15 | 58 | 22 |
| U.S. Pat. No. 5,693,795 | (VI) | Tubular reactor | n-BuOH | 290 | 4 | 85 * | 15 * |
| U.S. Pat. No. 6,512,114 | (VI) | Batch | Olio min. or DMA | 230 | 180 | 75 * 87.5* | 25 * 12.5* |

\* = Midazolam/Isomidazolam ratio only (other impurities not considered).

The product of the comparative experiments 4, 4-1, 4-2, 4-3 and of the two USA patents should be subjected to a further isomerisation process to reduce the high amount of Isomidazolam so as to be able to obtain Midazolam free of Isomidazolam after further crystallization, which would not be required for the product obtained according to the invention (examples 2 and 3).

Example 5

Synthesis of Climazolam of formula (VII)—Performed in Batch Mode—Example of the Invention Examples 1 and 2 were precisely repeated using the same moles of 8-chloro-6-(2-chlorophenyl)-1-methyl-4H-imidazo[1,5-a][1,4]benzodiazepine-3-carboxylic acid as the ones of the derivative of formula (VI) having fluorine instead of the chlorine in position 2'. Climazolam was obtained with 80% titre (determined via HPLC titre correcting it using the solvent) and containing 2% of Isoclimazolam.

Example 6

Synthesis of the compound of formula (V-bis)—Example of the Invention

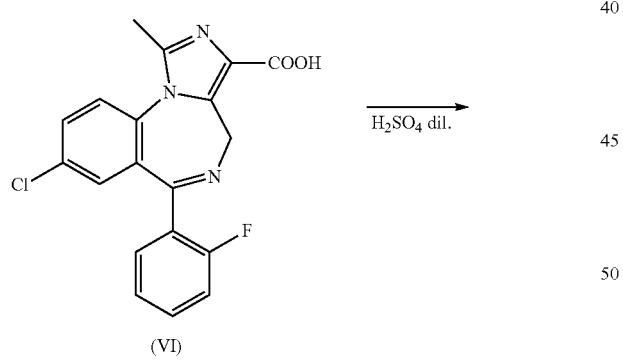

The preparation of Example 1 should be considered with the following modifications: diluted H2SO4 is used instead of diluted HCl, 5 volumes of EtOH with respect to substrate (VI), 2.5 equivalent moles of H2SO4 and, after precipitation of the product at 20/25° C., it is left stirring for 3 hours at the same temperature. The compound of formula (V-bis) is obtained with a molar yield of 98.60% and purity of 99.44% (HPLC A %).

$^1$H-NMR (300 MHz, d6-DMSO): 2.70 (s, 3H); 4.20 (d, 2H); 7.20-8.20 (m, 7H), 9.70 (sb, 4H).

Example 7

Synthesis of Midazolam of formula (IV)—Performed in Batch Mode—Example of the Invention The product obtained in example 6 is subjected to decarboxylation reaction in the same identical conditions used in example 3 obtaining—as the reaction product—Midazolam having a 68% titre (w/w) (determined via HPLC titre correcting it using a solvent) and containing 3% (w/w) of Isomidazolam.

Example 8

Preparation of 8-Chloro-6-(2-fluorophenyl)-1-methyl-4H-imidazo[1,5-a][1,4]benzodiazepine maleate (Midazolam Maleate)

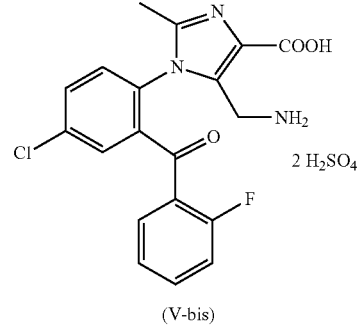

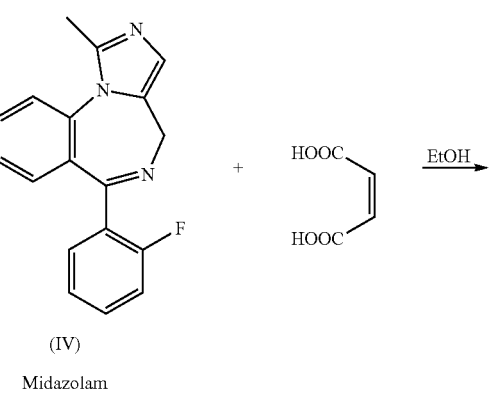

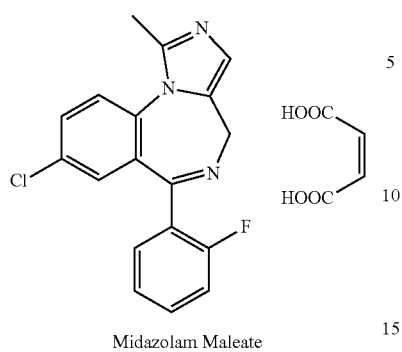

Midazolam Maleate

A 4-neck RBF was charged under nitrogen flow with: 10 g of Midazolam (IV) (prepared according to example 2) and 40 mL of Ethanol. The slurry was stirred until complete dissolution at 25/30° C. In an other flask was prepared the following solution: 3.72 g of maleic acid are dissolved in 15 mL of Ethanol. The slurry was stirred until complete dissolution at 25/30° C. The maleic acid solution is dropped in 30/40 minutes and keeping T=25/30° C. into the solution containing Midazolam. The slurry was cooled down at −15° C. in one hour and kept at that temperature for at least 2 hours. The slurry was then filtered and the cake was washed with 40 mL of cool Ethanol. The filter was discharged and the product was dried at 40° C. under vacuum for 2 hours and then at 60° C. for 8 hours. 12.8 g of Midazolam Maleate as white solid were collected (Molar yield=94.5%). m.p.=149-152° C. (by DSC).

Example 9

Preparation of 8-Chloro-6-(2-fluorophenyl)-1-methyl-4H-imidazo[1,5-a][1,4]benzodiazepine dihydrochloride (Midazolam dihydrochloride)

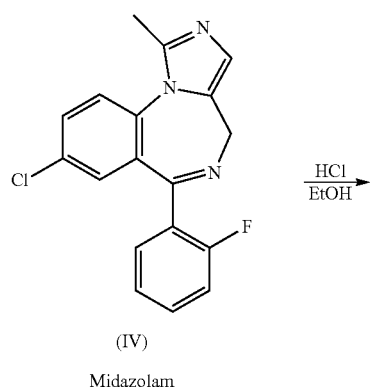

(IV)
Midazolam

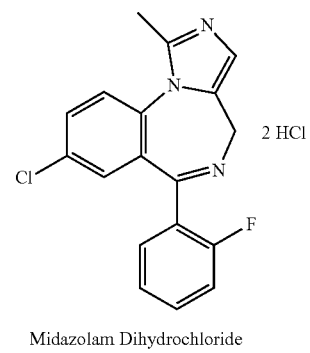

Midazolam Dihydrochloride

A 4-neck RBF was charged under nitrogen flow with: 1 g of Midazolam (IV) (prepared according to example 2) and 15 mL of Ethanol. The slurry was stirred until complete dissolution at 25/30° C. 5 mL of a ethanolic solution of Hydrochloric acid 2N were slowly added. 20 mL of Isopropanol were added over 30 minutes at RT. The slurry was cooled down at −15° C. in one hour and kept at that temperature for at least 2 hours. The slurry was then filtered and the cake was washed with 10 mL of cool isopropanol. The filter was discharged and the product was dried at 40° C. under vacuum for 2 hours and then at 60° C. for 8 hours. Midazolam dihydrochloride as white solid was collected.

Example 10

Preparation of 8-Chloro-6-(2-fluorophenyl)-1-methyl-4H-imidazo[1,5-a][1,4]benzodiazepine hydrochloride (Midazolam hydrochloride)

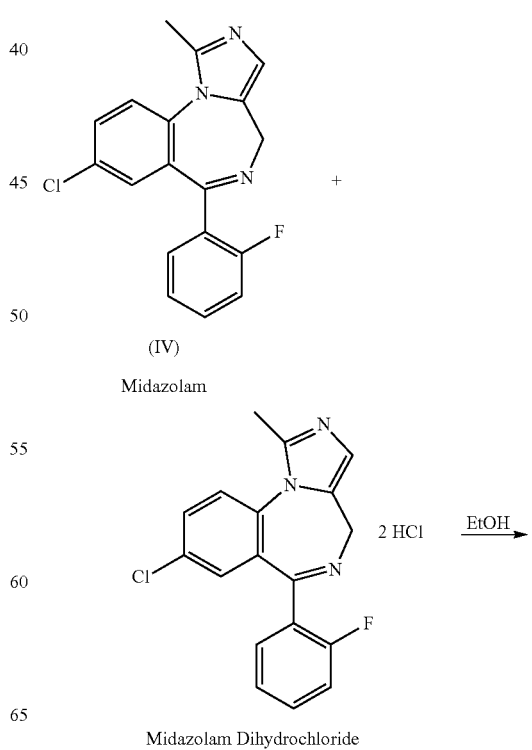

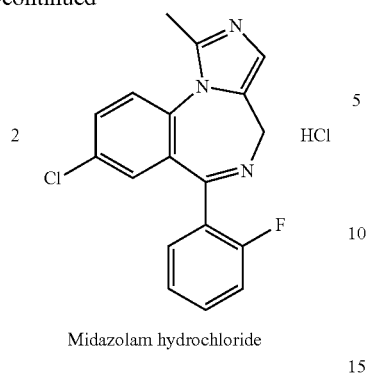

Midazolam hydrochloride

A 4-neck RBF was charged under nitrogen flow with: 1 g of Midazolam (IV) (prepared according to example 2) and 10 mL of Ethanol. The slurry was stirred until complete dissolution at 25/30° C. In an other flask was prepared the following suspension: 1.22 g of Midazolam dihydrochloride (prepared according to example 9) and 15 mL of Ethanol. The Midazolam ethanolic solution was added to the Midazolam dihydrochloride suspension. After filtration, the solution was treated with MTBE and heated at 60° C. until crystallization. After cooling to RT, the slurry was filtered, the cake washed with MTBE and the product was dried to provide Midazolam (mono)hydrochloride as a white solid.

In particular, it may be appreciated how the use of the selective decarboxylation process subject of the present invention allows obtaining 4H-imidazo[1,5-a][1,4]benzodiazepines, in particular Midazolam, avoiding the isomerisation step, with good yields and without requiring dedicated apparatus, without using drastic operative conditions, thus improving the operating capacity of the entire process.

The invention claimed is:

1. Process for the preparation of 4H-imidazo[1,5-a][1,4] benzodiazepine of formula (I) or a salt thereof:

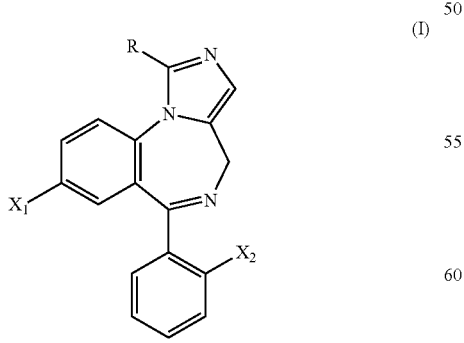

wherein R is selected from the group consisting of H, CH$_3$, CH$_2$OH and C$_2$H$_5$; X$_1$ and X$_2$ are independently selected from H and halogen;

comprising the following steps:
hydrolysis of the compound of formula (III):

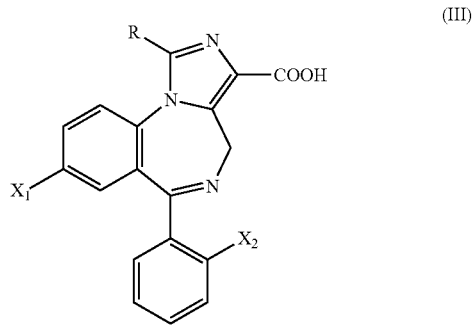

wherein R, X$_1$ and X$_2$ have the same meaning above specified,
to give the compound of formula (II)

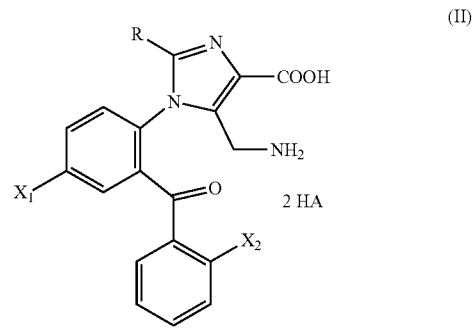

wherein HA is an inorganic acid,
decarboxylation of the compound of formula (II) to give the compound of formula (I) or a salt thereof.

2. Process according to claim 1 in which the step (b) comprises furthermore the following steps:
(b1) the conversion of the compound of formula (II) to the compound of formula (II-bis),

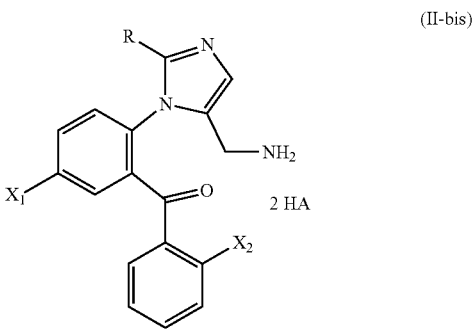

(b2) the conversion of the compound of formula (II-bis) to the compound of formula (I).

3. Process according to claim 2 in which the step (b2) is performed in presence of a base.

4. Process according to claim 1 for the preparation of Midazolam of formula (IV) or a salt thereof:

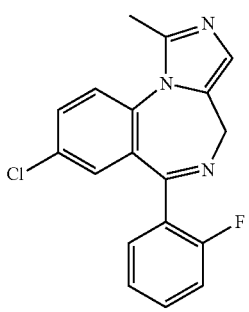

(IV)

comprising the following steps:

hydrolysis of the compound of formula (VI):

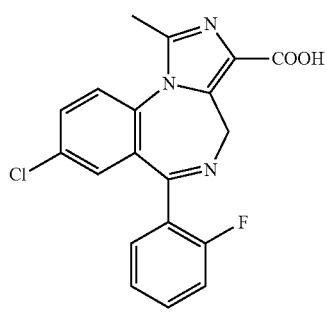

(VI)

to give the compound of formula (V)

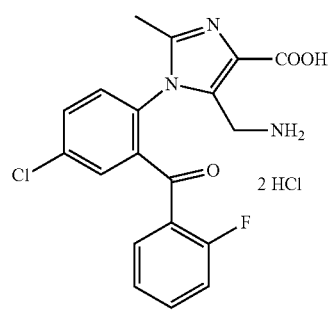

(V)

decarboxylation of the compound of formula (V) to give Midazolam of formula (IV) or a salt thereof.

5. Compound of formula (II):

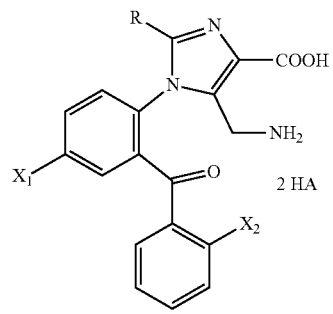

(II)

wherein R is selected from the group consisting of H, $CH_3$, $CH_2OH$ and $C_2H_5$; $X_1$ and $X_2$ are independently selected from H and halogen, and HA is an inorganic acid.

6. Compound according to claim 5 of formula (V):

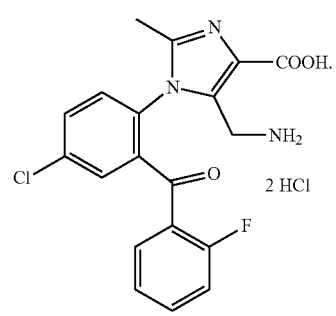

(V)

7. Process for the preparation of a compound of formula (I) or a salt thereof:

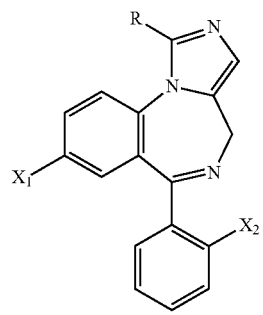

(I)

wherein R is selected from the group consisting of H, $CH_3$, $CH_2OH$ and $C_2H_5$; $X_1$ and $X_2$ are independently selected between H and halogen;

comprising the decarboxylation of the compound of formula (II)

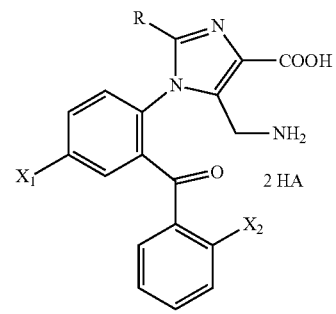

(II)

wherein R, $X_1$ and $X_2$ have the same meanings above specified and HA is an inorganic acid.

8. Process according to claim 7 in which R is methyl, $X_1$ is chlorine and $X_2$ is fluorine.

9. Process according to claim 1 wherein HA is selected from the group of hydrohalogenic acids and sulphuric acid.

10. Process according to claim 1 wherein the reaction of decarboxylation is performed in batch or in continuous by means of a microreactor.

11. Process according to any of claim 1 wherein the decarboxylation reaction is performed in NMP.

12. Process according to claim 1 wherein the decarboxylation reaction is performed at a temperature in the range from 150° C. to 250° C.

13. A method for the preparation of Midazolam of formula (IV) or a salt thereof:

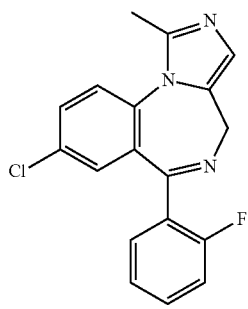

(IV)

comprising decarboxylation of the compound of formula (V)

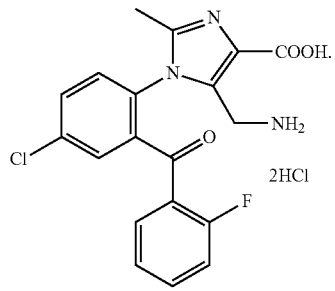

(V)

14. Process according to claim 1 wherein HA is hydrochloric acid.

15. Process according to claim 1 wherein the decarboxylation reaction is performed at a temperature in the range from about 180° C. to about 220° C.

* * * * *